(12) United States Patent
Baker et al.

(10) Patent No.: US 10,136,817 B2
(45) Date of Patent: *Nov. 27, 2018

(54) BODY AREA NETWORK PAIRING IMPROVEMENTS FOR CLINICAL WORKFLOWS

(71) Applicant: Welch Allyn, Inc., Skaneateles Falls, NY (US)

(72) Inventors: Steven D. Baker, Beaverton, OR (US); Braxton L. Lathrop, Lake Oswego, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/180,732

(22) Filed: Jun. 13, 2016

(65) Prior Publication Data

US 2016/0296116 A1 Oct. 13, 2016

Related U.S. Application Data

(63) Continuation of application No. 14/593,353, filed on Jan. 9, 2015, now Pat. No. 9,386,924, which is a continuation of application No. 12/827,817, filed on Jun. 30, 2010, now Pat. No. 8,957,777.

(51) Int. Cl.
*A61B 5/00* (2006.01)
*H04W 76/10* (2018.01)
(Continued)

(52) U.S. Cl.
CPC ............ *A61B 5/0024* (2013.01); *A61B 5/002* (2013.01); *A61B 5/7285* (2013.01);
(Continued)

(58) Field of Classification Search
CPC ..... H04W 48/14; H04W 48/16; H04W 76/02; H04W 84/18
(Continued)

(56) References Cited

U.S. PATENT DOCUMENTS

| 4,893,073 A | 1/1990 | McDonald et al. |
| 4,922,197 A | 5/1990 | Juds et al. |

(Continued)

FOREIGN PATENT DOCUMENTS

| EP | 0 589 466 A1 | 3/1994 |
| EP | 2 146 431 A2 | 1/2010 |

(Continued)

OTHER PUBLICATIONS

European Search Report for Application No. 12830143.9 dated Apr. 8, 2015, 9 pages.

(Continued)

*Primary Examiner* — Ping Hsieh
(74) *Attorney, Agent, or Firm* — Merchant & Gould P.C.

(57) ABSTRACT

A method for establishing a connection between a first electronic computing device and a second electronic computing device includes moving the second electronic computing device so that it is proximal to the first electronic computing device. When the first electronic computing device detects the proximity of the first electronic computing device relative to the second electronic computing device, a radio on the first electronic device is set to a connectable and discoverable state. A wireless connection is automatically established between the first electronic computing device and the second electronic computing device. Data is transmitted between the first electronic computing device and the second electronic computing device.

8 Claims, 6 Drawing Sheets

(51) Int. Cl.
*H04W 48/14* (2009.01)
*H04W 84/18* (2009.01)
*H04W 4/02* (2018.01)

(52) U.S. Cl.
CPC ........... *A61B 5/7425* (2013.01); *H04W 4/023* (2013.01); *H04W 48/14* (2013.01); *H04W 76/10* (2018.02); *H04W 84/18* (2013.01); *A61B 2560/0204* (2013.01); *A61B 2560/0214* (2013.01); *A61B 2560/0475* (2013.01); *A61B 2562/0223* (2013.01); *A61B 2562/0257* (2013.01); *A61B 2562/166* (2013.01)

(58) Field of Classification Search
USPC .................................... 455/41.1, 41.2, 41.31
See application file for complete search history.

(56) References Cited

U.S. PATENT DOCUMENTS

| | | |
|---|---|---|
| 4,994,738 A | 2/1991 | Soyck et al. |
| 5,326,945 A | 7/1994 | Gotoh et al. |
| 5,559,433 A | 9/1996 | Onizuka |
| 5,928,227 A * | 7/1999 | Howard, III ............ A61B 18/00 341/176 |
| 6,356,584 B1 | 3/2002 | Cuylen |
| 6,868,288 B2 | 3/2005 | Thompson |
| 6,934,874 B2 | 8/2005 | Retter et al. |
| 6,985,773 B2 | 1/2006 | Von Arx et al. |
| 7,042,364 B2 | 5/2006 | Capobianco et al. |
| 7,099,283 B2 | 8/2006 | Matta et al. |
| 7,197,357 B2 | 3/2007 | Istvan et al. |
| 7,424,288 B2 | 9/2008 | Jung et al. |
| 7,689,169 B2 | 3/2010 | Lee et al. |
| 7,860,456 B2 | 12/2010 | Kim |
| 7,973,657 B2 | 7/2011 | Ayed |
| 7,978,062 B2 | 7/2011 | LaLonde et al. |
| 8,179,124 B2 | 5/2012 | De Huu et al. |
| 8,907,782 B2 | 12/2014 | Baker |
| 8,957,777 B2 | 2/2015 | Baker et al. |
| 9,000,914 B2 | 4/2015 | Baker |
| 9,008,658 B2 | 4/2015 | Baker |
| 2002/0008625 A1 | 1/2002 | Adams et al. |
| 2002/0082480 A1 | 6/2002 | Riff et al. |
| 2003/0033032 A1 | 2/2003 | Lind et al. |
| 2003/0105499 A1 | 6/2003 | Hartley et al. |
| 2003/0142651 A1 | 7/2003 | Matta et al. |
| 2003/0149459 A1 | 8/2003 | Von Arx et al. |
| 2003/0206116 A1 | 11/2003 | Weiner et al. |
| 2004/0015058 A1 | 1/2004 | Besson et al. |
| 2004/0073127 A1 | 4/2004 | Istvan et al. |
| 2004/0102683 A1 | 5/2004 | Khanuja et al. |
| 2004/0202339 A1 | 10/2004 | O'Brien, Jr. et al. |
| 2004/0225199 A1 | 11/2004 | Evanyk et al. |
| 2004/0249257 A1 | 12/2004 | Tupin, Jr. et al. |
| 2004/0249258 A1 | 12/2004 | Tupin, Jr. et al. |
| 2005/0068173 A1 | 3/2005 | Capabianco et al. |
| 2005/0097191 A1 | 5/2005 | Yamaki et al. |
| 2005/0251680 A1 | 11/2005 | Brown et al. |
| 2005/0261556 A1 | 11/2005 | Such et al. |
| 2006/0025834 A1 | 2/2006 | Von Arx et al. |
| 2006/0115066 A1 | 6/2006 | Levien et al. |
| 2006/0135065 A1 | 6/2006 | Lee et al. |
| 2006/0179079 A1 | 8/2006 | Kolehmainen |
| 2006/0212085 A1 | 9/2006 | Fischell et al. |
| 2006/0219776 A1 | 10/2006 | Finn |
| 2006/0251256 A1 | 11/2006 | Asokan et al. |
| 2007/0003061 A1 | 1/2007 | Jung et al. |
| 2007/0010748 A1 | 1/2007 | Rauch et al. |
| 2007/0032832 A1 | 2/2007 | Feher |
| 2007/0070035 A1 | 3/2007 | Asbury et al. |
| 2007/0135866 A1 | 6/2007 | Baker et al. |
| 2007/0162089 A1 | 7/2007 | Mosesov |
| 2007/0264988 A1 | 11/2007 | Wilson, Jr. et al. |
| 2008/0005288 A1 | 1/2008 | Kodama et al. |
| 2008/0013601 A1 | 1/2008 | Lind et al. |
| 2008/0046039 A1 | 2/2008 | Corndorf |
| 2008/0052132 A1 | 2/2008 | Iliff |
| 2008/0140160 A1 | 6/2008 | Goetz et al. |
| 2008/0151695 A1 | 6/2008 | Kimmel et al. |
| 2008/0162183 A1 | 7/2008 | Sachanandani et al. |
| 2008/0165024 A1 * | 7/2008 | Gretton .............. G01C 21/3655 340/4.31 |
| 2008/0177150 A1 | 7/2008 | Li et al. |
| 2008/0183245 A1 | 7/2008 | Van Oort et al. |
| 2008/0183910 A1 | 7/2008 | Natoli et al. |
| 2008/0191866 A1 | 8/2008 | Falck et al. |
| 2008/0194922 A1 | 8/2008 | Holden |
| 2008/0227393 A1 * | 9/2008 | Tang .................... H04W 8/005 455/41.3 |
| 2008/0228045 A1 | 9/2008 | Gao et al. |
| 2008/0234557 A1 | 9/2008 | Demharter |
| 2008/0262376 A1 | 10/2008 | Price |
| 2008/0281169 A1 | 11/2008 | Akkermans et al. |
| 2008/0281170 A1 | 11/2008 | Eshelman et al. |
| 2008/0287748 A1 | 11/2008 | Sapounas et al. |
| 2009/0018453 A1 | 1/2009 | Banet et al. |
| 2009/0023391 A1 | 1/2009 | Falck |
| 2009/0030285 A1 | 1/2009 | Anderson |
| 2009/0043531 A1 | 2/2009 | Kahn et al. |
| 2009/0069642 A1 | 3/2009 | Gao et al. |
| 2009/0076343 A1 | 3/2009 | James et al. |
| 2009/0076348 A1 | 3/2009 | Manicka et al. |
| 2009/0076350 A1 | 3/2009 | Bly et al. |
| 2009/0088605 A1 | 4/2009 | Ross et al. |
| 2009/0096573 A1 | 4/2009 | Graessley |
| 2009/0112630 A1 | 4/2009 | Collins, Jr. et al. |
| 2009/0118595 A1 | 5/2009 | Greiner et al. |
| 2009/0140923 A1 | 6/2009 | Graves et al. |
| 2009/0215398 A1 | 8/2009 | Alder et al. |
| 2009/0222659 A1 | 9/2009 | Miyabayashi et al. |
| 2009/0227282 A1 | 9/2009 | Miyabayashi et al. |
| 2009/0231125 A1 | 9/2009 | Baldus et al. |
| 2009/0239587 A1 | 9/2009 | Negron et al. |
| 2009/0275296 A1 | 11/2009 | Huang et al. |
| 2009/0281399 A1 | 11/2009 | Keel et al. |
| 2009/0305212 A1 | 12/2009 | McKenzie et al. |
| 2009/0327713 A1 | 12/2009 | Marin et al. |
| 2010/0010322 A1 | 1/2010 | Brady |
| 2010/0010338 A1 | 1/2010 | van Dam et al. |
| 2010/0029205 A1 | 2/2010 | Lu et al. |
| 2010/0045425 A1 | 2/2010 | Chivallier |
| 2010/0081895 A1 | 4/2010 | Zand |
| 2010/0082983 A1 | 4/2010 | Shah et al. |
| 2010/0082990 A1 | 4/2010 | Grigorovitch |
| 2010/0104102 A1 | 4/2010 | Brown et al. |
| 2010/0125188 A1 | 5/2010 | Schilling et al. |
| 2010/0145165 A1 | 6/2010 | Merry |
| 2010/0160742 A1 | 6/2010 | Seidl et al. |
| 2010/0234720 A1 | 9/2010 | Tupin, Jr. et al. |
| 2010/0255782 A1 * | 10/2010 | Klemmensen ... H04N 21/43637 455/41.2 |
| 2010/0277304 A1 * | 11/2010 | Haartsen .............. G06F 1/3215 340/531 |
| 2010/0297946 A1 | 11/2010 | Alameh et al. |
| 2010/0331645 A1 * | 12/2010 | Simpson .............. A61B 5/0002 600/347 |
| 2011/0004072 A1 | 1/2011 | Fletcher et al. |
| 2011/0004073 A1 | 1/2011 | Corroy et al. |
| 2011/0015496 A1 | 1/2011 | Sherman et al. |
| 2011/0018854 A1 | 1/2011 | Barclay et al. |
| 2011/0028091 A1 * | 2/2011 | Higgins .............. H04L 63/0492 455/41.2 |
| 2011/0040345 A1 | 2/2011 | Wenzel et al. |
| 2011/0105861 A1 | 5/2011 | Derchak et al. |
| 2011/0125535 A1 | 5/2011 | Gross |
| 2011/0137133 A1 | 6/2011 | Espina Perez |
| 2011/0152632 A1 | 6/2011 | Le Neel et al. |
| 2011/0160786 A1 | 6/2011 | Stubbs et al. |
| 2011/0183698 A1 | 7/2011 | Hoctor et al. |
| 2011/0202371 A1 | 8/2011 | Darguesse et al. |
| 2011/0208015 A1 | 8/2011 | Welch et al. |
| 2011/0210820 A1 | 9/2011 | Talty et al. |

(56) References Cited

U.S. PATENT DOCUMENTS

| | | | |
|---|---|---|---|
| 2011/0213216 A1* | 9/2011 | McKenna | A61B 5/0002 600/301 |
| 2011/0221590 A1 | 9/2011 | Baker et al. | |
| 2011/0288379 A1 | 11/2011 | Wu | |
| 2012/0001751 A1 | 1/2012 | Baker et al. | |
| 2012/0003933 A1 | 1/2012 | Baker et al. | |
| 2012/0158428 A1 | 6/2012 | Nuthi | |
| 2012/0220835 A1 | 8/2012 | Chung | |
| 2014/0128674 A1 | 5/2014 | Wieters | |
| 2015/0050888 A1 | 2/2015 | Baker et al. | |
| 2015/0164326 A1 | 6/2015 | Baker et al. | |

FOREIGN PATENT DOCUMENTS

| | | |
|---|---|---|
| JP | 61-149820 A | 7/1986 |
| JP | 4-84948 A | 3/1992 |
| JP | 2010-027611 A | 2/2010 |
| KR | 10-2009-0011863 | 2/2009 |
| KR | 10-2009-0059324 A | 6/2009 |
| WO | 2006047400 A2 | 5/2006 |
| WO | 2008/033970 A2 | 3/2008 |
| WO | 2010/029086 A | 3/2010 |
| WO | 2011115717 A1 | 9/2011 |

OTHER PUBLICATIONS

Ultra Wideband RFID, Safe, Secure and Interference-Free, Technical Note, http://www.timedomain.com/datasheets/UWBInterference.pdf, 1 page (Apr. 16, 2009).

Versel, "How Mobile Health can Abide by HIPAA," Mobihealthnews, http://mobihealthnews.com/10747/how-mobile-health-can-abide-by-hipaa/ (Apr. 20, 2011).

International Search Report and Written Opinion in PCT/US2012/051830 dated Feb. 1, 2013, 10 pages.

Antoniou et al.; "iTouch: RFID Middleware for Boosting Connectivity & Intuitive User Interaction in Smart Spaces," May 9, 2006, 34 pages.

U.S. Appl. No. 12/723,726, filed Mar. 15, 2010.

Cho et al.; Opportunistic Medical Monitoring Using Bluetooth P2P Networks, Jun. 2008, 6 pages.

Kostelnik et al.; Blue Medica—Wireless Medical Data Access Appliance, 2008, 7 pages.

Agrafioti et al.; On Supporting Anonymity in a Ban Biometric Framework; Digital Signal Processing, Aug. 18, 2009; © 2009 IEEE; 6 pages.

Chowdhury et al.; Context-aware Data Association and Authenticity in Pervasive Healthcare; Dec. 1, 2009; © 2009 IEEE Computer Society; pp. 227-230.

Falck et al.; Plug 'n Play Simplicity for Wireless Medical Body Sensors; Mobile Netw Appl, vol. 12 Issue 2-3, Jul. 25, 2007; © Springer Science + Business Media, LLC; pp. 143-153.

International Search Report and Written Opinion in PCT/US2011/024853, dated Aug. 2, 2011, 10 pages.

Olla: Mobile Health Technology of the Future: Creation of an M-Health Taxonomy Based on Proximity; Int. J. Healthcare Technology and Management, vol. 8, Nos. 3-4; © 2007 Inderscience Enterprises Ltd.; pp. 370-387.

U.S. Appl. No. 12/827,817, filed Jun. 30, 2010.

U.S. Appl. No. 13/225,989, filed Sep. 6, 2011.

\* cited by examiner

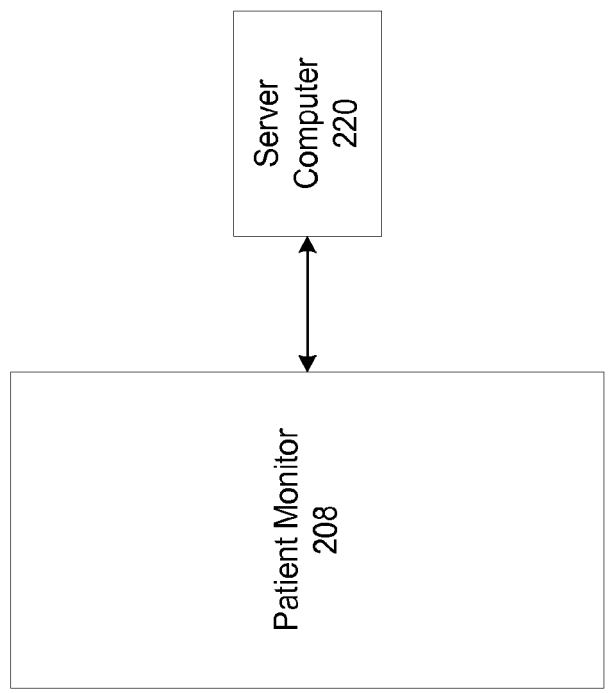
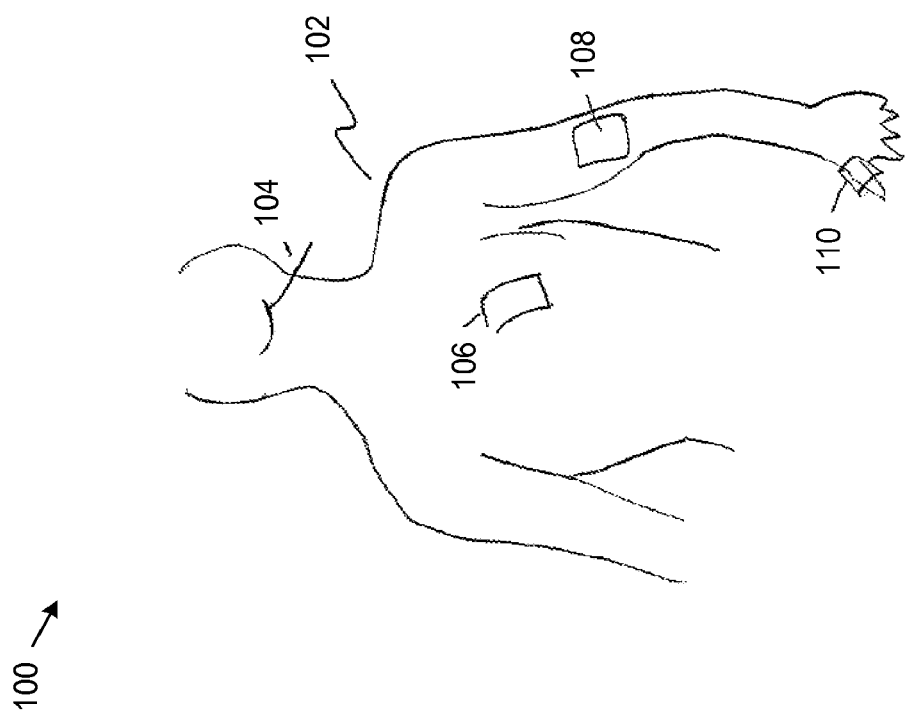
FIG. 1

BODY AREA NETWORK PAIRING IMPROVEMENTS FOR CLINICAL WORKFLOWS

CROSS REFERENCE TO RELATED APPLICATION

This application is related to U.S. patent application Ser. No. 12/723,726, titled "Personal Area Network Pairing" and filed Mar. 15, 2010, the contents of which are incorporated herein by reference.

BACKGROUND

Personal area networks in a medical setting permit sensor data from a patient to be efficiently transmitted to a display device. These networks typically use Bluetooth technology both in sensors attached to the patient and in the display device. Each Bluetooth sensor is typically paired to the display device to enable the transmission of sensor data to the display device.

In order for a Bluetooth sensor to be paired to a display device, power must be applied to both the Bluetooth sensor, including the sensor radio, and the display device including, the display device radio. Each radio must be in a connectable mode. Further, if the radios in the sensor and display device are not aware of each other, the radios must also be in a discoverable state. Typically, Bluetooth sensors operate on battery power. It is desirable that a mechanism for applying power to a Bluetooth sensor be easy to use, minimize drainage of the battery, connect to the desired display device and ensure that the patient be correctly identified.

SUMMARY

Aspects of the disclosure are directed to establishing a connection between a first electronic computing device and a second electronic computing device. The second electronic computing device is moved so that the second electronic computing device is proximal to the first electronic computing device. The first electronic computing device detects the proximity of the first electronic computing device relative to the second electronic computing device. When the first electronic computing device detects the proximity of the first electronic device relative to the second electronic computing device, a radio on the first electronic computing device is set to a connectable and discoverable state. A wireless connection is established between the first electronic computing device and the second electronic computing device. Data is transmitted between the first electronic computing device and the second electronic computing device.

In another aspect, a medical sensor device includes a system memory, a processing unit, a physiological sensor, a radio device, a housing, a printed circuit board, a proximity detector and a power source. The physiological sensor is attached to a patient in a medical facility. The physiological sensor monitors one or more types of physiological data from the patient. The radio device establishes a wireless connection to a patient monitoring device. The physiological data from the patient is transmitted from the medical sensor device to the patient monitoring device via the wireless connection. The power source is configured to switchably provide power to the medical sensor device. The actuation of the proximity detector causes the radio device to be placed in a connectable state.

In another aspect, a patient monitoring device includes a system memory, a processing unit, a display unit, a radio device, a network interface to a server computer, a housing, a printed circuit board and a proximity detector. The display unit displays medical data from one or more patients in a medical facility. The radio device is capable of establishing a wireless connection to a physiological sensor device for a patient in the medical facility. The radio device receives physiological data from the patient via the wireless connection. The physiological data from the patient is transmitted to the server computer via the network interface. The radio device establishes the wireless connection to the physiological sensor device after the proximity detector actuates at a predetermined threshold.

The details of one or more techniques are set forth in the accompanying drawings and the description below. Other features, objects, and advantages of these techniques will be apparent from the description, drawings, and claims.

DESCRIPTION OF THE DRAWINGS

FIG. 1 shows an example personal area network for a medical application.

DETAILED DESCRIPTION

Figure 2:
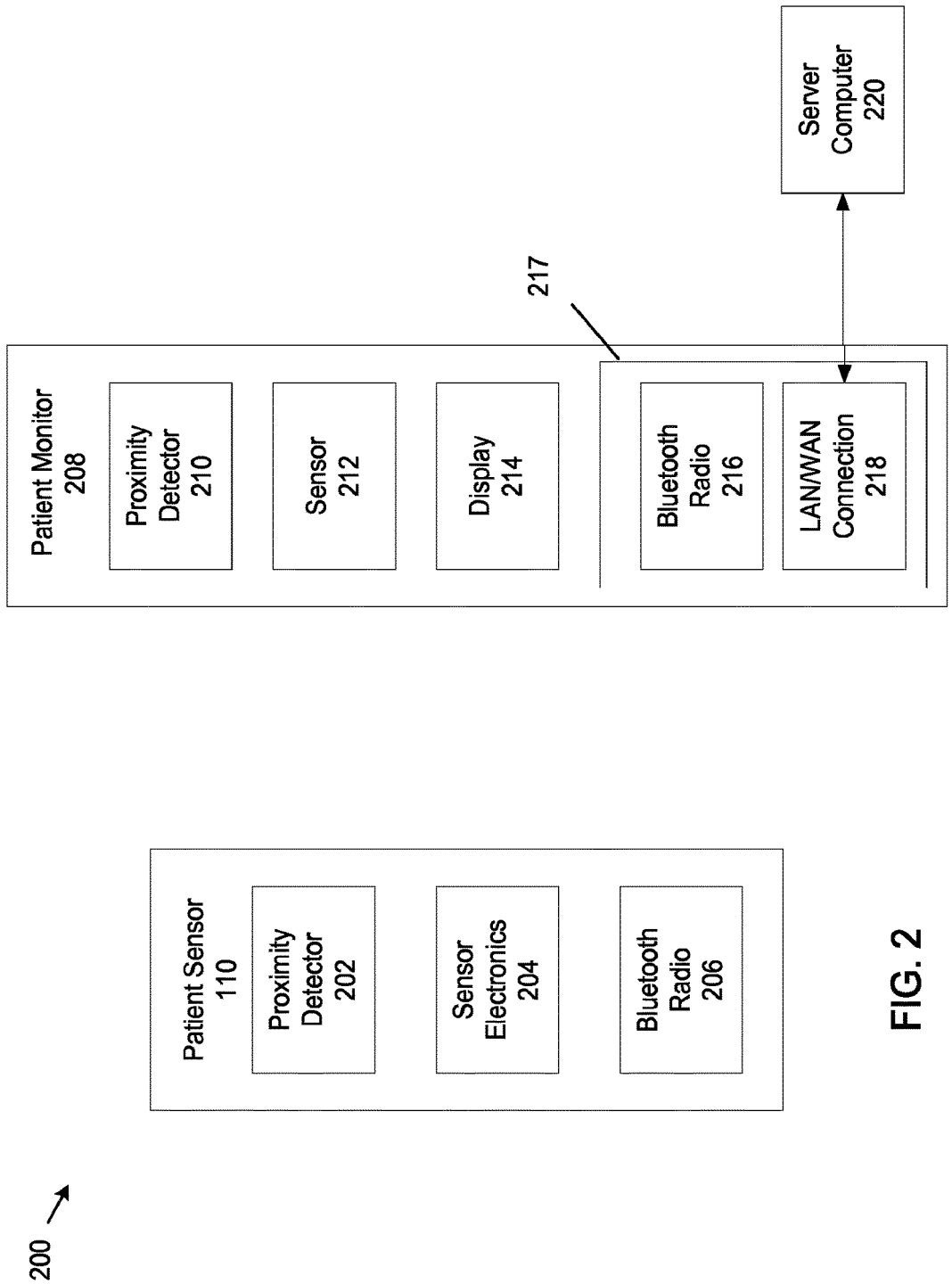
FIG. 2 shows example modules of a physiological sensor and of the patient monitor of FIG. 1.

The present disclosure is directed to example systems and methods for pairing physiological sensor devices for a patient in a personal area network. In the systems and methods, a proximity detector is used to enable devices to execute functions such as turning on power at a sensor device, turning on power to a radio in the sensor device, and enabling the radio device to making a radio connection between devices. The proximity detector turns the power on at the sensor device when the sensor device is in close proximity to a gateway device. The gateway device is typically a monitoring and display device that also provides access to a local or wide area network for transmitting sensor data to a server computer. The gateway device also includes a proximity detector. Typically, the gateway device includes a source of AC power so that the gateway device is generally powered on. However, in other examples, the gateway device may be battery operated and may not be powered on until the gateway device comes into proximity with a sensor device.

In example embodiments, the proximity detector on the sensor device provides a magnetic mechanism to activate power at the sensor device. Each proximity detector includes both a magnet and a magnetic detector. When the proximity detector on the sensor device is in close proximity with the proximity detector on the gateway device, the magnetic detector on the gateway device detects the magnet on the sensor device and the magnetic detector on the sensor device detects the magnet on the gateway device.

The detection of the magnet by the sensor device activates power on the sensor device and the detection of the magnet on the gateway device provides an indication to the gateway device that power is activated on the sensor device. In examples where the gateway device does not include AC power or in cases where the gateway device does include AC power but is powered off, the detection of the magnet on the gateway device activates power on the gateway device. Once power is activated on both the sensor device and the gateway device, a Bluetooth pairing sequence is initiated and the sensor device is paired to the gateway device.

If either the sensor device or the gateway device is already powered, then the proximity detection may power the radio, enable the radio and put the radio in a connectable state. If the radio in either the sensor device or the gateway device is already powered, then the proximity detection may put the radio in a connectable state.

Other proximity detectors may be used. If each device has a coil, magnetic coupling allows the coil in one device to detect if the coil in the other device has a current. One could pulse current in the first coil and detect the current pulse in the second coil. Detection of the current pulse in the coil of the first device by the coil of the second device would indicate proximity. A related solution with a magnet and a coil in the first device and a magnetic detector and a coil on the second device could have the second device detect proximity of the first device through actuation of the magnetic switch. The proximity detection causes the second device to enable its radio and also to pulse a current through its coil. This current pulse is detected in the first device, causing it to enable its radio. Alternately, placing a load on the receiving coil allows the transmitting coil to detect proximity of the receiving coil as reflected impedance of the receiving coil's load affects the current and voltage in the transmitting coil. Proximity detection may be accomplished through time stamps of related signals, such as acceleration when two devices are tapped together. A time stamp on the signals can be used as a filter to ensure that the two devices were tapped at close to the same time. Alternately, a device may require a specific sequence such as three taps before enabling the radio. Optical signals (IR, UV, or Visible) from one device may be received by the second and these could be both detected by the second device and be reflected back to the first device. By encoding the optical signal, one may confidently assume the signal is authentic. A resistive detection could be used to detect if one device touches another as could one-wire serial where making electrical contact causes one device to transmit data to the other, such as a Bluetooth address and other out of band communication. Capacitive touch switches may be placed on a printed circuit board or embedded in the plastic cases creating a hidden switch that is activated when a hand is brought nearby. Ultrasonic transceivers, Ultra-Wideband (UWB) and RFID may be used for both proximity detection and communication of out of band data. For example, UWB can be used to determine if the range between two radios is less than 25 cm and only then allow the radios to connect.

The systems and methods of the present disclosure may also use contextual data to determine when to change the radio state to connectable or connectable and discoverable. For example, a sensor may assume that it is in range of a gateway whenever the sensor is powered, whenever a new measurement is requested or when other contextual events occur and automatically put its radio in a discoverable and connectable state. Other contextual events include one or more of: losing connection to a previous gateway, detecting a new gateway, detecting a decrease in received power from the current gateway, detecting an increase in received power from a new gateway and receiving new patient information.

A personal area network is a computer network used for communication between computer devices close to an individual person. A personal area network may also be referred to as a body area network when the personal area network is a collection of physiological sensors and monitors. In this disclosure, pairing refers to Bluetooth pairing and also to equivalent transmission of credentials and information, such as an address, required to establish a radio connection. These credentials may include authentication credentials, such as public keys and nonces that may be used to authenticate devices for secure, authenticated data transfer.

In a medical setting, a personal area network may include physiological sensor devices attached to a patient that are used to monitor health parameters of the patient. Some examples of physiological sensor devices used in a medical setting are blood pressure monitoring devices, thermometers, ECG sensors, EEG sensors, cardiac output sensors, $ETCO_2$ sensors, and oxygen saturation sensors ($SPO_2$). Other types of sensor devices can be used. The sensor devices typically transmit sensor data over a network to a patient monitoring device, such as a wall-mounted display unit or a central station, such as the ACUITY® Central Monitoring System from Welch Allyn Inc. of Skaneateles Falls, N.Y. A personal area network may also include a Personal Digital Assistant (PDA), perhaps used by a clinician to interact with the patients' personal area networks such as the Clinician Notifier product from Welch Allyn Inc. of Skaneateles Falls, N.Y. The PDA could join a patient network either using a menu-based system as is common for Bluetooth connections today or it could have a proximity detector that causes the PDA to joint the personal area network.

One type of radio device used in a wireless personal area network is a Bluetooth radio. Bluetooth is a wireless technology that can be used in personal area networks to transmit and receive data over short distances (generally less than 30 feet, although data can be transmitted up 100 meters depending on device class). Bluetooth uses a layered protocol architecture consisting of four core layers and associated protocols. The physical layer is the lowest layer in each Bluetooth device and is instantiated as a radio frequency ("RF") layer that includes a transceiver with transmit and receive capability. Bluetooth uses the microwave radio spectrum in the 2.402 GHz to 2.4835 GHz range.

Bluetooth devices are peer devices, each including a Bluetooth radio and the four core protocol layers. However, when two or more Bluetooth devices are connected in a personal area network, one device can become a master device and the remaining devices then become slave devices. A master Bluetooth device can communicate with up to seven slave devices. However, a slave can switch roles and become a master at any given time. A Bluetooth device may be a slave in one personal area network and a master in a second personal area network. Later version of the Bluetooth specification, such as Bluetooth LE, provide for a larger set of peer devices.

Because Bluetooth is a wireless technology, the integrity and privacy of the transmitted data are a concern. To improve the integrity and privacy of data transmission, Bluetooth permits two devices to be paired with each other where the devices transmit on an encrypted link so that they can securely communicate with each other. Once two devices are paired, they can connect and communicate with each other without additional user intervention. The pairing process is typically initiated the first time a device receives a connection request from a device to which it is not already paired. During the discovery process Bluetooth addresses of each device are shared and during the pairing process, a shared secret key, known as a link key, is generated by the two devices. This link key is used to generate an encryption key, which is used to encrypt data for the current session. If the link key is stored along with the Bluetooth address of the peer device, then the devices are bonded so that the pairing information can be used in the future, even if the device(s) has been power cycled or if the devices have been out of range of each other. If either device deletes the link key, pairing must occur again before communication can occur. At the start of each communication session, the link key is used in a process to cryptographically authenticate the identity of the device, and be sure that it is the same device with which it previously paired.

In a wireless personal area network, sensor data is transmitted using a wireless data exchange protocol, such as Bluetooth, to a central point, called a hub. Often, this central point has a connection to a larger network, such as an 802.3 or 802.11 LAN. A hub with a connection to a different type of network is called a bridge.

In a wireless personal area network for monitoring sensor data, each sensor device may be joined to the network. In Bluetooth, joining a network when none of the network information is known requires discovery to learn the Bluetooth address of the other device, connection to initiate communication, and pairing to generate a shared secret key for authentication and encryption. While this disclosure uses Bluetooth as an example personal area network, any network, including 802.15.4, Bluetooth LE, ZigBee, UWB, a low-power 802.11 network, Wi-Fi™ Direct, or a proprietary network could be used. Other physical media such as IR as disclosed in the IEEE 802.11-1999 standard and ultrasonic may be used in lieu of RF. Of these, some technologies allow for ranging and ranging allows proximity detection. These include at least UWB, IR, and Ultrasound.

A hub to which multiple sensors are paired that includes a display to show the physiological state of the patient is a patient monitoring device. This type of hub typically has a local area network uplink, making the patient monitoring device a bridge. Any RF enabled device with a processor and display, including a PDA, cellular phone, PC, or laptop can operate as a hub and also as a patient monitor. The appropriate pairing of a sensor device with a patient monitoring device ensures that the sensor data is properly transmitted to the correct monitoring device. This is particularly important in a medical setting that may include a plurality of patients, sensors, monitoring devices and personal area networks to ensure that a particular patient's physiological data is tagged with his patient identifier. The patient identifier may be encrypted independent of any encryption that occurs automatically on the communication link to further ensure protection of electronic personal health information.

The procedure for pairing a sensor device to a monitoring device typically requires a user to manually enter data to authenticate that the proper devices are connecting in order to complete the pairing. For example, using Bluetooth 2.0, the two devices that pair require that the same PIN is presented to both devices. For some limited functionality devices, such as headsets, the PIN for the headset may be hard coded into the headset and the user enters the PIN into the device to be paired, e.g., a cellular telephone. Since no data are transacted prior to PIN entry and the PIN is not transmitted, this process verifies that the user intends the two devices to establish a connection. This solution works reasonably well if the device is only to be paired once. The PIN solution also has security and usability issues, particularly as implemented. For example, the PIN for most headsets is an easy to remember number such as 0000 or 9999, so an intruder can guess the PIN and masquerade as the intended device. In addition, a brute force attack requires only 10,000 different sequences (Although Bluetooth 2.0 uses a 16-byte PIN, this is usually generated by augmenting a 4-digit PIN with part of the Bluetooth address of the device, which is known). If the use case requires pairings to be made, removed, and re-built as occurs in clinical applications, the time to enter the PIN and navigate menus may be cumbersome. The systems and methods described in the present disclosure permit sensor devices to be attached to a patient and paired to a monitoring device in an efficient and automated manner, thereby minimizing the need for a user to manually enter information.

An improved pairing mechanism introduced in Bluetooth Version 2.1+EDR is Secure Simple Pairing (SSP). SSP has four modes of operation: Numeric Comparison, Passkey Entry, Out-Of-Band (OOB), and Just Works. With the first two modes, some degree of user intervention is required to either enter or compare numeric values that are computed as a function of the link key. In the third mode, an auxiliary set of transceivers must exist to transmit the Bluetooth pairing information. In the fourth mode, the devices assume that a user authentication step occurred and opens the device to a security risk, such as a man-in-the-middle (MITM) attack. This risk can be mitigated by only placing the devices in a pairing mode when proximity is detected and also through application level filtering of the devices. For example, if the radios are neither connectable nor discoverable, except for a few seconds while the pairing information is exchanged, it is extremely unlikely an eavesdropper could detect the Personal Area Network (PAN) and generate a MITM attack before the pairing completes. If an incorrect device pairs, application level software can cause the radio to delete pairing information and destroy the RF connection. Such deletion and destruction can occur before any data are accepted across the RF link. Application level software can determine correct device pairings through several methods including comparing the Bluetooth address to a known list of acceptable addresses, through an application level challenge-response or other authentication solution.

FIG. 1 shows example physiological sensors that can be used on a patient 100 in a personal area network for a medical application. The four physiological sensors include an example thermometer 104, ECG sensor 106, blood pressure sensor 108 and SPO$_2$ sensor 110. The SPO$_2$ sensor is also known as an oxygen saturation sensor. The sensors 104, 106, 108, and 110 can be paired to patient monitor 208 and communicate with a medical application over a personal area network, as described below.

FIG. 2 shows an example personal area network 200 for a medical application. The example personal area network 200 includes the example SPO$_2$ sensor 110 and an example patient monitor 208. The example personal area network 200 may also include one or more of the example physiological sensors 104, 106 and 108 (shown in FIG. 1). Each of the example physiological sensors 104, 106, 108, 110 has Bluetooth capability. The example SPO$_2$ sensor 110, as well as the example sensors 104, 106 and 108, also includes a proximity detector 202, sensor electronics 204 and a Bluetooth radio 206.

The example patient monitor 208 includes a proximity detector 210 and may include one or more embedded sensors 212 that have a physical attachment to patient monitor 208. The patient monitor also includes a display 214 that indicates the state of various sensors and network connections. In addition, the patient monitor 208 includes a Bluetooth radio 216 and a LAN/WAN connection 218, providing a gateway 217. The LAN/WAN connection 218 permits data to be transmitted between the example personal area network 200 and one or more server computers 220 that are accessible via the LAN/WAN connection. Other network connections including mesh, UWB, MAN and the like may allow connection to the one or more server computers 220.

Typically, the example physiological sensors 104, 106, 108, 110 are not powered on until they are activated and placed on the patient. The example patient monitor 208 is may be continually powered on. For example, the patient monitor 208 may be a wall-mounted unit or may be permanently mounted to a stand or other apparatus in hospital room. When the patient monitor 208 is permanently mounted, the patient monitor 208 typically is connected to AC power and is typically continually powered on. Alternatively, the patient monitor 208 may be a portable unit that is operated via battery power. When the patient monitor 208 is a portable unit, the patient monitor is typically powered on manually via a power-on button. However, in examples, a portable patient monitor may also be power on automatically via the proximity detector 210.

In order for Bluetooth pairing to occur, Bluetooth devices must be both discoverable and connectable. By using a proximity detector in a Bluetooth device, for example physiological sensor 110, the Bluetooth device may be kept in a low power state to save power until the Bluetooth device is moved into close proximity with a second Bluetooth device, for example patient monitor 208.

In some examples described herein, the physiological sensor 110 is off. In other examples, the physiological sensor 110 can be in a low power state including any of the following: the physiological sensor 110 being completely off, the microprocessor of physiological sensor 110 operating in a low power mode, the radio in physiological sensor 110 being in a low power mode, the radio in physiological sensor 110 being on, but not in a connectable state, or the radio in physiological sensor 110 being off. Regardless of the state of the physiological sensor 110 and its radio, detection of another proximal device causes the physiological sensor 110 and its radio to move to a state where the radio can connect to another device.

When the physiological sensor 110 is moved proximally to the patient monitor 208, power is turned on at the physiological sensor 110, power is turned on at the patient monitor 208 if power is not already turned on at the patient monitor 208, the radios on both the physiological sensor 110 and the patient monitor 208 are placed in connectable and discoverable mode, and Bluetooth pairing occurs between the physiological sensor 110 and the patient monitor 208. The Bluetooth pairing establishes a wireless connection between the physiological sensor 110 and the patient monitor 208. Note that if sensor 110 and patient monitor 208 have previously paired and bonded, the radios do not need to discover each other. Similarly, if the sensor 110 and patient monitor 208 have been provisioned with the pairing information, perhaps at manufacturing, the radios do not need to discover each other. Once paired to the patient monitor 208, the physiological sensor 110 is placed on the patient 100 and physiological data is sent from the physiological sensor 110 to the patient monitor 208 via the wireless connection. For a body-worn patient monitor 208, pairing may occur after the sensor is placed on the patient 102 and pairing may occur after the patient monitor 208 is placed on the patient 102.

Providing an auxiliary, low power discovery permits the medical device to be selective in the devices with which it might connect. For example, upon detection of an auxiliary discovery signal, the radio may change state to "discoverable" or "discoverable and connectable" for a limited time so that only the opportunity to connect to the wrong device is decreased compared to a device that is always in the "discoverable" or "discoverable and connectable" state. If both sides of the connection have this feature, then the opportunity to connect to the wrong device is further diminished. When one device is AC powered, the radio may be kept in connectable and discoverable mode all the time and rely on the physiological sensor 110 to correctly initiate pairing. However, if the device is always in a connectable and discoverable state, the opportunity is open for either the wrong device or a malevolent device to connect. Alternately, the AC powered device may exit discoverable mode, but stay in connectable mode. This allows another sensor, perhaps that has lost contact with its primary gateway, to send physiological data via an alternate gateway. Even if this other sensor does not have a patient ID, a unique identifier such as the sensor serial number can be associated to the patient. With this unique identifier, sensor data transmitted via an alternate gateway can be associated with the correct patient ID at the server computer 220. Another case for keeping radios in connectable mode allows re-connections to occur. Once a physiological sensor is communicating with a patient monitor, each will likely keep its radio in connectable mode, but not discoverable mode. This allows the two devices to re-connect if the RF link is broken, but does not allow any other devices to discover the PAN. To keep the network more secure but still allow devices to reconnect, the devices may also exit both discoverable and connectable states after connecting to sensors and upon loss of RF connection move to the connectable state.

As devices connect to different gateways, the status of those devices, including location, need for periodic maintenance, battery status, software revision and the like may be annotated to a server for use by the biomedical engineers and clinicians. After Bluetooth pairing is completed, status and configuration information are transferred between sensor device and gateway device, for example between physiological sensor 110 and patient monitor 208, to verify that both the sensor device and the gateway device are operational and compatible with each other. For example, application software of patient monitor 208 may query physiological sensor 110 to verify that physiological sensor 110 has passed a diagnostics self test, to verify the strength of a battery on physiological sensor 110, to determine if any component of physiological sensor 110 is in need of repair or due for periodic maintenance, or to determine the status of the RF connection. This status information may be transmitted along with other parameters from the monitor such as its own RF connection strength to the IT network, battery status, and location. These data may be used to trend performance, debug connection issues, or to determine if maintenance is required. In addition to the status information, the sensor provides model and version information. The model and version of the sensor device are compared with the model and version of the gateway device to determine whether the sensor device and gateway device are compatible.

When the sensor device and the gateway device are paired, the sensor device and the gateway device are said to have a logical connection with each other that is analogous to the connection that occurs when a cable is plugged into the monitor. This logical connection may occur at an RF level or at an application level. For example, the logical connection may occur at the RF level after the devices are paired or the logical connection may occur at the application level when the compatibility check between devices is completed. In the cable analogy, plugging the cable into the device is analogous to the RF connection and the device recognizing the cable and the sensors at the end of that cable are analogous to a connection at the application level.

After status and compatibility are checked and verified between sensor and gateway devices, a clinician is required to verify the sensor device for a specific patient. Requiring the clinician to confirm the sensor device for a specific patient provides an additional level of security to ensure that the sensor device is placed on the correct person. In addition, the clinician must confirm the sensor for a specific patient within a short time period after the sensor device and the gateway device are placed in connectable and discoverable modes. Through confirming the device the clinician indicates to the system that the data from the new sensor belongs to the same patient as is indicated on the patient monitor. If the clinician does not confirm the sensor for a specific patient within the short time period, the wireless connection between the sensor device and the gateway device is broken and the logical connection between the sensor device and the gateway device is destroyed. The reset of the logical connection might include removal of the pairing information. By allowing pairing for only a short time period after the sensor device and the gateway device are placed in connectable and discoverable modes, MITM attacks are minimized. The time period must last long enough for both radios to enter the connectable state and connect or to enter the connectable and discoverable state, be discovered, and connect. A short time period may be range from a hundred milliseconds to several seconds. Preferably, the radio exits the connectable state or the connectable and discoverable state immediately upon initiation of a radio connection. Leaving the logical connection in place could allow the sensor to maintain a connection to the incorrect monitor. The system may be configured to allow the unconfirmed connection to remain; but without indicating the patient ID. In this case, a pseudo-ID may be used to identify the data until such time as a patient ID is assigned to the sensor. For example, the data might be saved in a database keyed by the sensor serial number instead of the patient ID. If the sensor is later correctly connected to the proper patient monitor, the data that has been thus far collected and stored is annotated with the patient ID associated with the proper patient monitor.

After the clinician confirms the sensor device for a specific patient, the clinician selects a connection mode for the connection between the sensor device and the gateway. The connection mode describes the extent to which alarms and equipment alerts are generated in the connection. An alarm refers to an error condition for a patient while an equipment alert refers to an error condition for the medical equipment. Application software at the gateway device permits the clinician to assign one of three connection modes—loose pairing, tight pairing and locked. Each connection mode is defined to match a specific workflow and provides a class of alarm response. For example, loose pairing provides one class of alarm response, tight pairing provides a second class of alarm response and locked provides a third class of alarm response. Other application-level connection modes and combinations thereof may be used to match different workflows.

Loose pairing is typically used for a spot monitoring workflow in which a sensor device is periodically brought into a patient's room to check a physiological parameter that is not being monitored by the patient monitor in the patient's room. This is sometimes referred to as spot checking. In a workflow that uses loose pairing, there are no equipment alerts if the connection between the sensor device and the gateway device is broken. There may also be no alarms as the workflow includes a clinician at the patient location.

Tight pairing is typically used for a workflow in which there is continuous monitoring of patient physiological data. In a tight pairing connection, an equipment alert is generated whenever certain error conditions occur. For example, an equipment alert is generated when the wireless connection between the sensor device and the gateway device is broken. This is analogous to an equipment alert if an ECG cable is removed from the monitor or the ECG electrode falls off the patient. Another error condition that causes an alarm to be generated is when the gateway device determines that one or more physiological parameters received from the sensor device is above or below a predetermined threshold. Other error conditions that cause an equipment alert condition to be generated include: need for maintenance (including scheduled periodic maintenance), sensor device loss of power, unacceptable RF performance such as high packet loss or poor signal level, RF interference, inappropriately sized blood pressure cuff detected, ECG lead failure, $SPO_2$ sensor with no signal detected, a sensor that is not confirmed for a particular patient, and other equipment alerts familiar to those skilled in the art.

When an error condition occurs in the tight pairing connection mode where the connection from the patient to the device comes into question, in addition to an alarm being generated, the wireless connection between the sensor device and the gateway device may be broken and pairing information for the connection may be deleted at the sensor device and at the gateway device. For example, if a physiological sensor falls of the patient, when the physiological sensor is re-attached, the clinician may be required again connect the Bluetooth radios. The deletion of pairing information when the connection is broken prevents physiological data from the sensor device from being associated with an erroneous patient identification number. Alternately, the application level software may allow the Bluetooth connection to persist, but stop annotation of the data with the patient ID until the patient ID is confirmed. A system may also stop the data flow from the sensor until the patient ID is confirmed. The system may have a record of the data and use an algorithm such as pattern recognition to verify the sensor is still attached to the same patient or the system may correlate the physiological signal from the unconfirmed sensor with physiological data from a confirmed sensor to determine if they are still on the same patient. If the data correlates, the system may begin annotating data from the previously unconfirmed sensor.

Locked pairing is used when it is determined that a sensor device is only to be connected to a specific gateway device, for example to the patient monitor 208 or to a select set of gateway devices. When a sensor device is used with locked pairing, an equipment theft alert is generated when an attempt is made to connect the sensor device to a gateway device that is not included in the select set of gateway devices. The intent of a locked connection is to minimize the potential for the sensor device from being moved, borrowed or stolen from the gateway device to which the sensor device is connected. To allow the locked sensor device to be moved to a different gateway, as may be the case when the original gateway is damaged or has a dead battery, a reset capability is designed into the product. This may be through a hidden service screen, a reset button, through a specific set of key strokes or similar method that obscures the ability to remove the locked pairing configuration.

Figure 3:
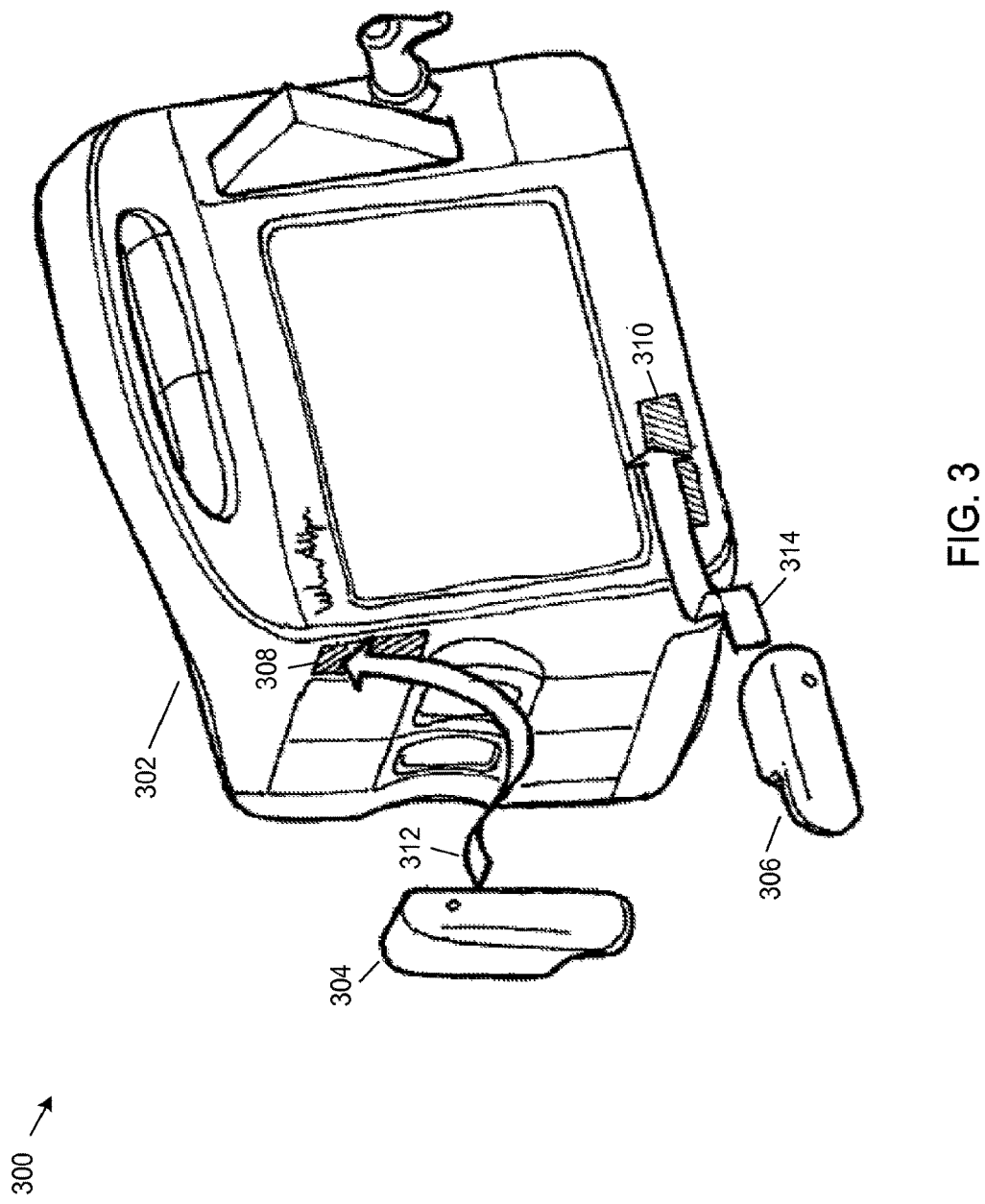
FIG. 3 shows an example patient monitor that includes a proximity detector.

FIG. 3 show an example patient monitor 300. The example patient monitor 300 is a portable device and includes two example proximity detectors 308 and 310. The proximity detectors 308 and 310 are mounted internally in the patient monitor 300 with one surface of each of proximity detectors 308 and 310 being adjacent to an external surface of the patient monitor 300.

Also shown in FIG. 3 are two example physiological sensor devices 304, 306, each including a proximity detector, for example proximity detector 202. Arrow 312 shows the direction in which physiological sensor device 304 is moved to become in close proximity with proximity detector 308. Arrow 314 shows the direction in which physiological sensor device 306 moves to become in close proximity with proximity detector 310. In examples, more or fewer proximity detectors may be used and the proximity detectors may be located on different areas of the patient monitor 300.

Figure 4:
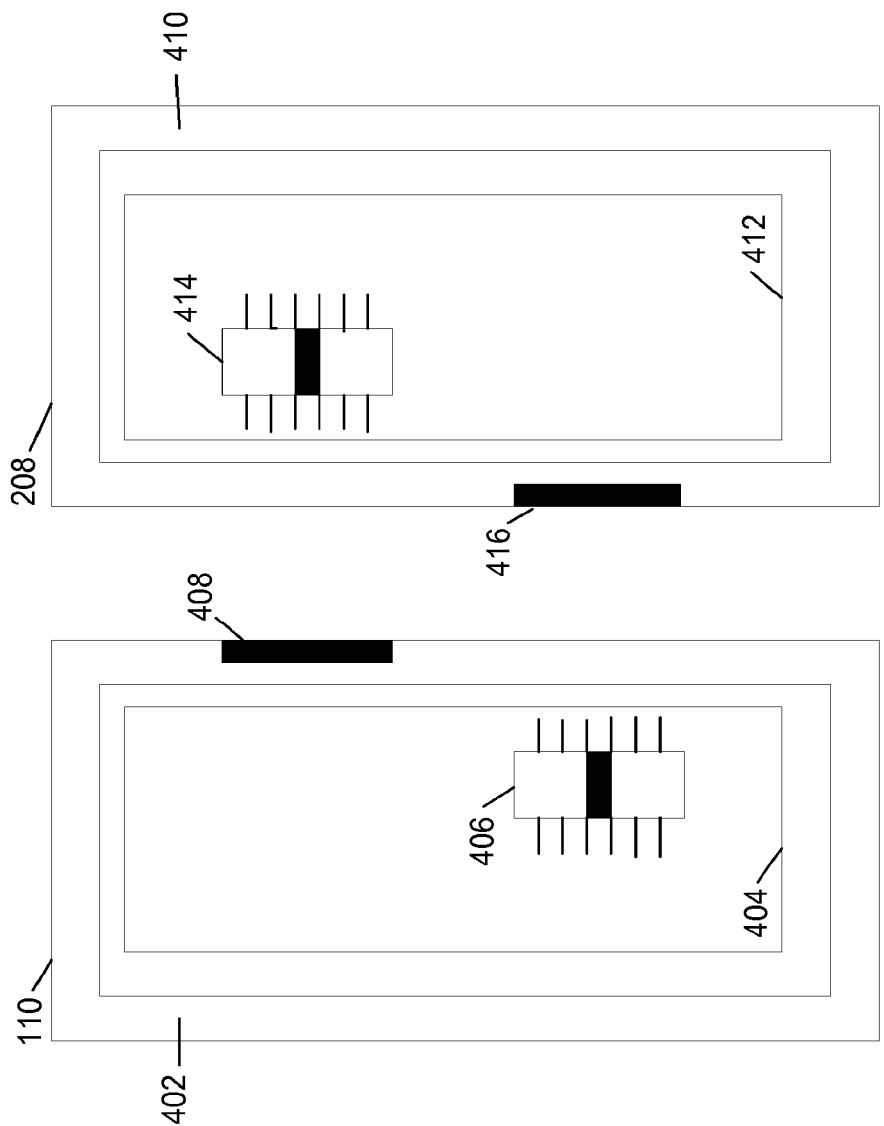
FIG. 4 shows example components of the proximity detector of FIG. 3.

FIG. 4 shows an example physical view for the proximity detection mechanism for physiological sensor 110 and proximity detector 202. Physiological sensor 110 is housed in a plastic housing 402 and includes a printed circuit board (PCB) 404 that includes sensor electronics 204 and Bluetooth radio 206 (not shown), a magnet 408 and a magnetic detector 406. The magnet 408 and magnetic detector 406 comprise proximity detector 202. Patient monitor 208 is housed in a plastic housing 410 and includes a printed circuit board 412, a magnet 416 and a magnetic detector 414. The magnet 416 and magnetic detector 414 comprise proximity detector 210. Patient monitor 208 includes the Bluetooth radio 216 (not shown). When physiological sensor 110 is moved into close proximity with patient monitor 208, magnet 408 on physiological sensor 110 activates magnetic detector 414 in patient monitor 208 and magnet 416 on patient monitor 208 activates proximity detector 406 on physiological sensor 110.

The magnetic detectors 406, 414 are typically a magnetic switch such as a reed switch, a reed relay, a Hall Effect sensor, a Hall Effect switch or a giant magnetoresistance (GMR) detector. These magnetic switches permit proximity detection using very low power.

The reed switch is a normally open switch, thereby drawing little or no power in the open state. The reed switch closes when a magnetic field of a predetermined threshold is detected by the reed switch. A typical threshold for a sensitive reed switch may vary between 5 Ampere-Turns and 15 Ampere-Turns. However, this assumes a uniform magnetic field along the axis of the axially leaded part.

A Hall effect sensor generates a voltage in response to a magnetic field. The generated voltage increases as the magnetic field increases. For example, when a magnet is moved in the proximity of the Hall effect sensor, the magnetic field of the magnet cutting through the sensor increases as the magnet is moved closer to the Hall effect sensor. The Hall effect sensor may be combined with circuitry such as a comparator that permits the Hall effect sensor to act as a switch. When the magnetic field reaches a predetermined threshold, a magnetic switch closes, signifying an "on" state. A sensitive Hall effect sensor may operate at field strengths of around 10 to 25 Gauss, depending on temperature and frequency of the magnetic field.

A GMR switch includes giant magnetoresistance material and makes use of the concept of magnetoresistance. With magnetoresistance the electrical resistance of the GMR material changes its value when a magnetic field is applied to it. When the magnetic field reaches a predetermined threshold, the resistance of the GMR material is changed to a point such that sufficient current flows through a bridge in the GMR switch to close the GMR switch, signifying an "on" state. Some GMR switches, for example GMR switches in the AFL200 series from NVE Corporation, require only a few microamperes of supply current. A sensitive GMR switch may operate at a field strength of 7-13 Gauss.

Whether the magnetic switch is normally open or normally closed is not relevant to the detection of an applied magnetic field; rather only the state change is important.

Magnetic flux densities decrease in strength exponentially with increasing distance from the source of the magnetic field, for example a magnet. The magnet 408 must be strong enough to activate magnetic detector 414 when physiological sensor 110 is brought in the proximity of the magnetic detector 414. However, at the same time, the magnet 408 must be positioned so that the magnet 408 does not falsely trigger magnetic detector 406 or any other magnetic detectors in other medical devices that may be implanted on a patient. For example, implantable cardio defibrillators may have embedded magnetic detectors that are typically activated at a field strength of greater than 10 Gauss. However, in order to create a magnetic field that is reliably detectable by magnetic detector on a patient monitor 208, magnet 408 and magnet 416 may need to provide a magnetic field or more than 10 Gauss.

Each magnet 408, 416 is located on the outside of their respective plastic housing 402, 410. Each magnet 408, 416 is recessed in the plastic housing 402 and positioned so that one side of each magnet 408, 416 is flush with a side of the plastic housing 402. The reason magnets 408 and 416 are located on the outside on their respective plastic housing 402, 410 is to permit the use of a weaker magnet than would be needed if the magnets 408 and 416 were located within their plastic housing. The reason for this is the exponential decrease in magnetic flux density with distance. Suppose a magnet were placed on the inside of the plastic and had sufficient magnetization to create a field of 10 Gauss at 4 mm outside the plastic. Comparing to a magnet recessed as indicated by magnets 408 and 416 that has sufficient magnetization to create a field of 10 Gauss at 4 mm from the outside of the plastic, the latter magnet would be weaker and its field strength at more than 4 mm from the outside of the plastic will be less than the field strength of the stronger magnet placed inside of the plastic.

Using a weaker magnet minimizes the risk of false triggers for medical devices that contain embedded magnetic detectors. Placing magnets 408 and 416 on the outside of their respective plastic housings places magnet 408 closer to magnetic detector 414 than would be the case if magnet 408 were located inside of plastic housing 402 and places magnet 416 closer to magnetic detector 406 than would be the case if magnet 416 were located inside of plastic housing 410. Typically, the spacing gap between magnets 416 and magnetic detector 406 and between magnet 408 and magnetic detector 414 is reduced by 2 millimeters by placing magnets 408 and 416 on the outside of their respective plastic housings.

Physical detents may be included in the plastic housing to help the user properly locate the sensor 110 relative to monitor 208 to trigger the proximity detection. Labels may be used over the magnets 408 and 416 and over the magnetic detectors 406 and 408 to help guide the user to place the physiological sensor 110 in proper alignment with the magnetic detector in monitor 208.

Figure 5:
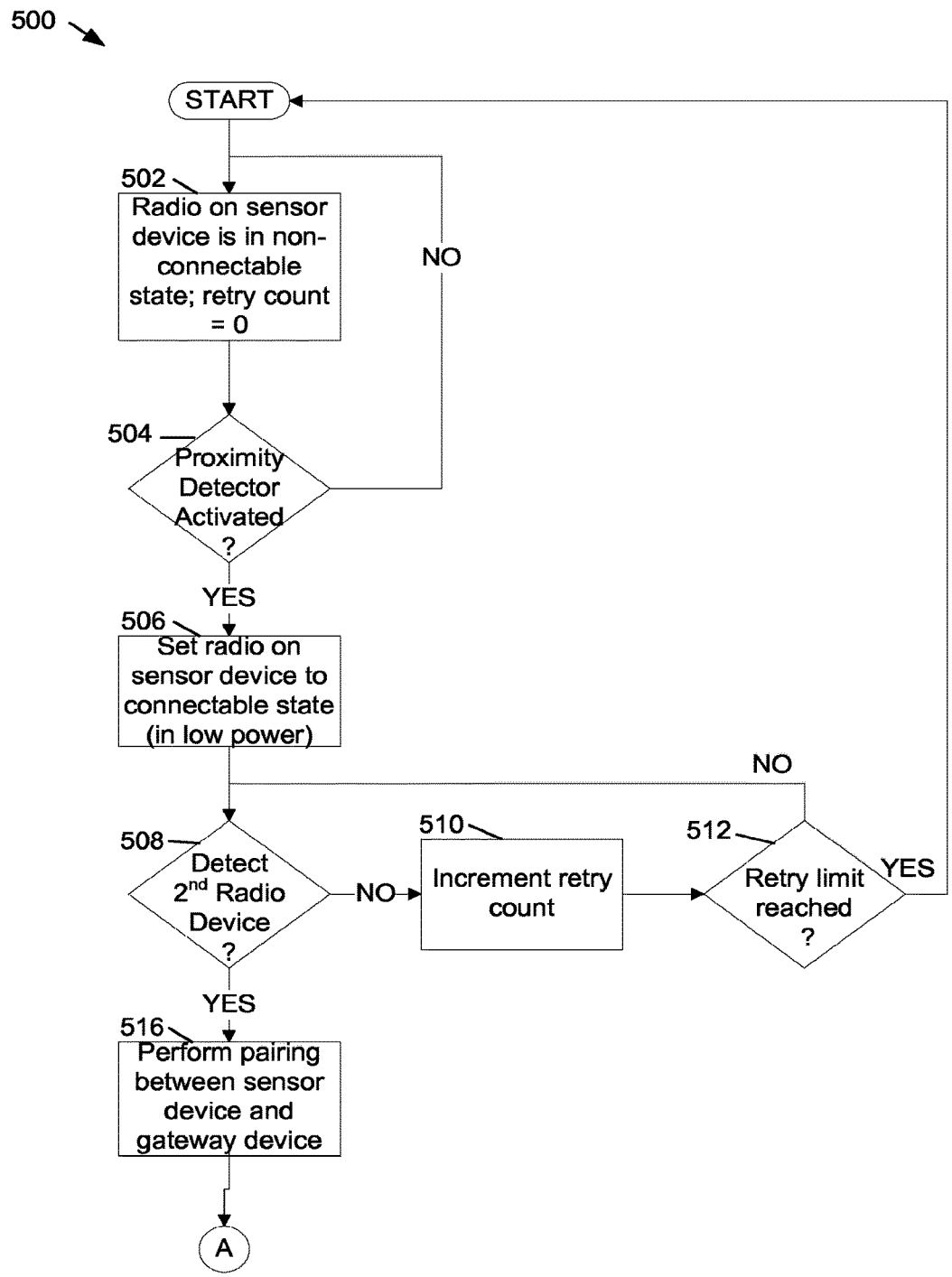
FIGS. 5 and 6 show a flowchart for a method of establishing a connection between a sensor device and a gateway device in the personal area network of FIG. 2.
Figure 6:
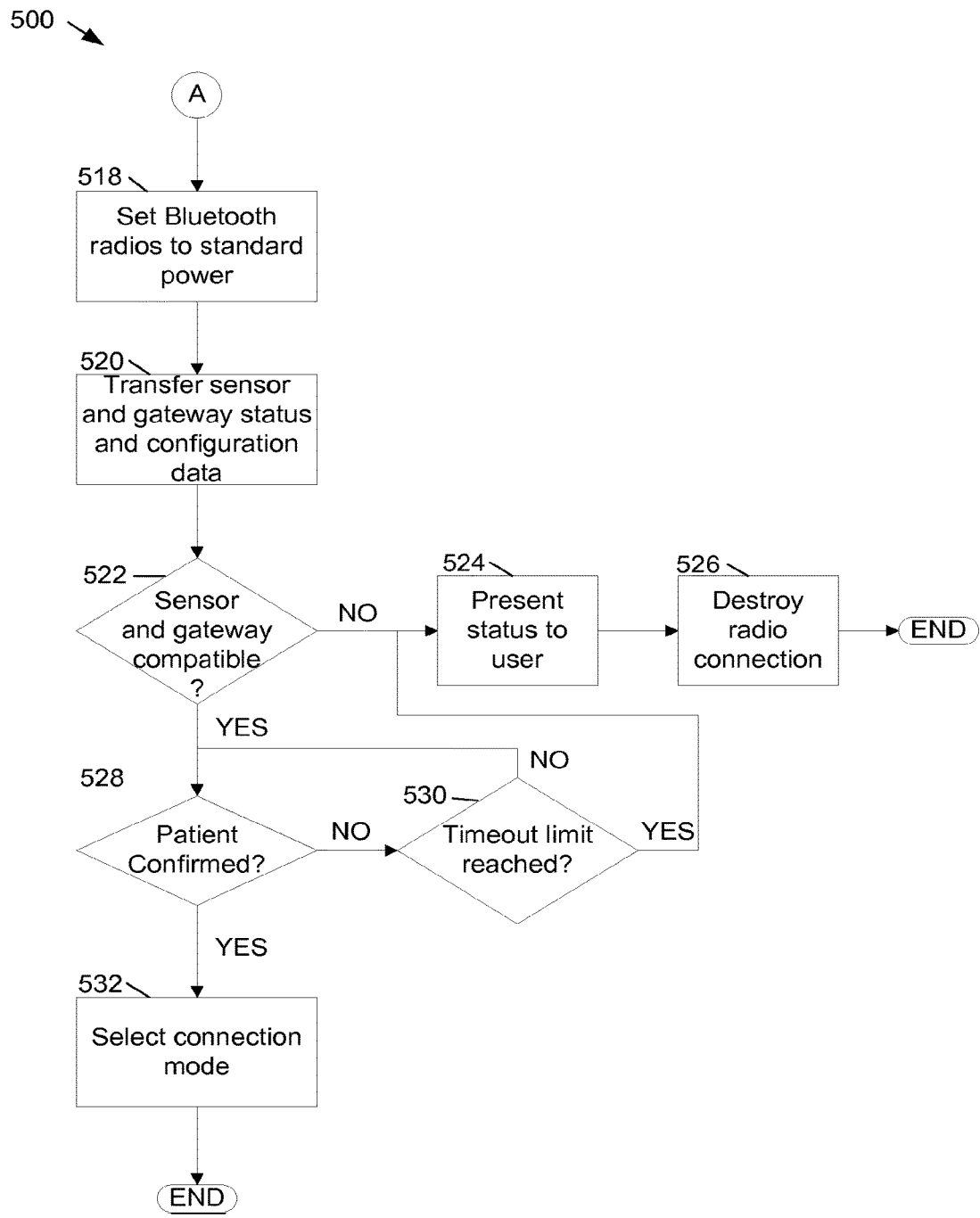

FIGS. 5 and 6 show a flowchart 500 for a method for establishing a connection between a sensor device, for example physiological sensor 110 and a gateway device, for example patient monitor 208. At operation 502, a radio on the sensor device is in a non-connectable state. Typically, both the radio and the sensor device are powered off. An internal retry count is set to zero.

At operation 504, a determination is made whether a proximity detector on the sensor device is activated. The proximity detector on the sensor device is typically not activated until the sensor device is proximal to the gateway device. The determination of whether the proximity detector is activated comprises whether a magnet, for example magnet 416 on the gateway device activates a magnetic detector, for example magnetic detector 406 on the sensor device. Depending on the strength of the magnet on the gateway device, the sensor device may need to be moved within centimeters of the gateway device or in some examples the sensor device may need to physically touch the gateway device in order for the magnetic detector to be activated.

When a determination is made at operation 504 that the proximity detector is not activated, control loops back to operation 502. Control loops between operation 502 and operation 504 until the proximity detector is activated.

When a determination is made at operation 504 that the proximity detector is activated, at operation 506, the Bluetooth radio on the sensor device is set to a connectable state, in low-power. This includes powering on the radio if it was not powered. The use of low-power radio transmission during connection improves security during the connection process, but is not required.

At operation 508, a determination is made as to whether the sensor device detects a second radio device, for example a Bluetooth radio, on the gateway device and whether the gateway device detects a radio device on the sensor device. Typically, proximity detection occurs near simultaneously at sensor device and the gateway device and each places its respective radio in a connectable state. This connectable state may include also being discoverable. However, the Bluetooth radio on the gateway device may turn on at a slightly different time than the Bluetooth radio on the sensor device. It is also possible that one magnetic detector was triggered and the other was not.

If a determination is made at operation 508 that a second Bluetooth radio is not detected, typically because there is a slight delay in turning on power for the second Bluetooth radio, at operation 510 a retry count is incremented. At operation 512, a determination is made as to whether a retry limit has been reached. When it is determined at operation 512, that a retry limit has not been reached, control returns to operation 508 and another determination is made as to whether a second Bluetooth radio has been detected. When it is determined at operation 512, that a retry limit has been reached, control returns to operation 502 and the sensor device is put back in a non-connectable state. Alternatively, instead of a fixed number of retries, a determination may be made at operation 512 as to whether a timeout limit has been reached.

When a determination is made at operation 508 that a second Bluetooth radio has been detected, at operation 516, Bluetooth pairing is performed between the sensor device and the gateway device.

At operation 518, the radio devices are set to a standard power level and the sensor device is paired to the gateway device. For example, standard power is 4 dBm for a Class II Bluetooth radio and 20 dBm for a Class I Bluetooth radio.

At operation 520, status and configuration information are transferred between the sensor device and the gateway device. The status and configuration includes such items as the strength of a battery on the sensor device and the model and version numbers of the sensor device and the gateway device. The status and configuration information are transferred in an attempt to determine whether the sensor device is operationally compatible with the gateway device.

At operation 522, a determination is made as to whether the sensor device and the gateway device are compatible. The determination is made by comparing the model number and version of the sensor device with the model number and version number of the gateway device to a file or database indicating the set of compatible versions and models.

When it is determined at operation 522 that the sensor device and the gateway device are not compatible, at operation 524, a status message that the sensor device and gateway device are not compatible is displayed to the user. This status message might be displayed on the gateway device, the sensor device, a syslog server, through e-mail or other electronic communication. At operation 526, the logical connection between the sensor device and the gateway device is broken and the connection sequence ends. Breaking the logical connection might be at the application layer or at the RF layer and might include removing stored pairing information. The incompatibility message may be sent to a server.

When it is determined at operation 522 that the sensor device and the gateway device are compatible, at operation 528, a message that the sensor device and the gateway device are compatible is displayed on the user interface of the gateway device and the clinician is prompted to confirm the patient for the sensor device. The confirmation of the patient to the sensor device provides an additional level of security to ensure that the sensor device is being assigned to the correct patient.

If there is no confirmation determined at operation 528, at operation 530, a determination is made as to whether the allotted wait time for the clinician has expired. If a timeout occurs, meaning that the clinician has not confirmed the patient for the sensor device within a reasonable period of time, at operation 524, a message is displayed on the user interface of the gateway device that the patient has not been confirmed for the sensor and at operation 526, the logical connection between the sensor device and the gateway device is broken. At operation 530, if the timeout limit has not been reached, then control is returned to operation 528.

When the patient has been confirmed for the sensor device, at operation 532, the connection mode is selected. As discussed, the connection mode can be one of loose pairing, tight pairing or locked. Additional connection modes may be created to support additional clinical work flows.

A physiological sensor and monitor that incorporate Bluetooth technology are computing devices and typically include at least one processing unit, system memory and a power source. Depending on the exact configuration and type of computing device, the system memory may be physical memory, such as volatile memory (such as RAM), non-volatile memory (such as ROM, flash memory, etc.) or some combination of the two. System memory typically includes an embedded operating system suitable for controlling the operation of the sensor device. The system memory may also include one or more software applications, for example Bluetooth, and may include program data.

The various embodiments described above are provided by way of illustration only and should not be construed to limiting. Various modifications and changes that may be made to the embodiments described above without departing from the true spirit and scope of the disclosure.

What is claimed is:

1. A method for connecting a sensor device to a patient monitoring device, the method comprising:
    setting a first radio of the sensor device to off;
    detecting when the sensor device is in proximity of the patient monitoring device;
    upon detecting proximity of the patient monitoring device, turning on the first radio of the sensor device;
    before pairing, detecting a second radio of the patient monitoring device;
    after turning on the first radio of the sensor device and after detecting a second radio of the patient monitoring device, pairing the first radio of the sensor device to the second radio of the patient monitoring device;
    transferring status information and configuration information to the patient monitoring device;
    determining whether the sensor device is compatible with the patient monitoring device;
    providing an indication if the sensor device is not compatible with the patient monitoring device; and
    selecting a connection mode between the sensor device and the patient monitoring device, the connection mode being one of:
        loose pairing that provides no alerts when a connection between the sensor device and the patient monitoring device is broken, and
        tight pairing that provides the alerts when the connection between the sensor device and the patient monitoring device is broken.

2. The method of claim 1, further comprising detecting the proximity of the patient monitoring device using at least one magnet.

3. The method of claim 2, further comprising turning on the first radio in a lower-power mode when the proximity is detected.

4. The method of claim 1, further comprising turning on the first radio in a lower-power mode when the proximity is detected.

5. The method of claim 1, further comprising setting the first radio in a standard power mode before pairing the first radio of the sensor device to the second radio of the patient monitoring device.

6. The method of claim 1, wherein the connection mode further includes locked pairing that provides the alerts when an unapproved sensor is connected to the patient monitoring device.

7. The method of claim 1, further comprising using the loose pairing to conduct a spot monitoring workflow.

8. The method of claim 1, further comprising using the tight pairing to conduct a continuous monitoring workflow.

* * * * *